US006019471A

United States Patent [19]

Thorne et al.

[11] Patent Number: 6,019,471

[45] Date of Patent: Feb. 1, 2000

[54] VISUAL AID, STORAGE MEDIUM AND METHOD

[75] Inventors: Sherry C. Thorne; Thomas L. Thorne, Jr., both of Greensboro, N.C.

[73] Assignee: Starline, Inc., Greensboro, N.C.

[21] Appl. No.: 09/086,644

[22] Filed: May 29, 1998

[51] Int. Cl.[7] .......... A61B 3/00

[52] U.S. Cl. .......... 351/200

[58] Field of Search .......... 156/249, 247; 428/13, 14; 40/594, 773, 774, 745, 746; 351/200

[56] References Cited

U.S. PATENT DOCUMENTS

| | | | |
|---|---|---|---|
| 3,024,553 | 3/1962 | Rowley | 156/249 |
| 4,231,833 | 11/1980 | Lieberman | 156/249 |
| 4,640,030 | 2/1987 | Wood et al. | 40/746 |
| 4,662,093 | 5/1987 | Suttles et al. | 40/773 |

*Primary Examiner*—George Manuel

[57] ABSTRACT

This invention comprises a thin polyethylene film with a tacky adhesive ply removably positioned on a storage medium comprising a paper planar member with at least one non-stick surface. The film includes a transparent section and an opaque section. Using the film comprises releasably adhering the film to an item and viewing the item through the transparent section.

18 Claims, 3 Drawing Sheets

VISUAL AID, STORAGE MEDIUM AND METHOD

BACKGROUND OF THE INVENTION

1. Field of the Invention

This invention pertains to a visual aid for use with a cross-stitch pattern, a storage medium for holding the same and a method.

2. Description of the Prior Art and Objectives of the Invention

Cross-stitching is a popular activity for people of all ages. It relieves stress and provides a productive outlet for energy culminating in an attractive usable or framable article. Unfortunately for those with imperfect vision or failing eyesight, concentrating on an intricate pattern can be difficult, especially large complex patterns.

At other times, it is desirable to have a mechanism which effectively, selectively highlights or outlines a portion of a larger item. While adhesive backed markers, labels, peel-off tape and other devices are conventionally available, their generally opaque nature limits their effectiveness in many respects from serving as a suitable visual aid.

Thus, with the above concerns and needs in mind, it is an objective of the present invention to provide a visual aid which selectively, removably highlights or outlines portions of a larger item such as a cross-stitch pattern.

It is a further objective of the present invention to provide a visual aid which includes a plurality of border ticks to further facilitate the highlighting function.

It is still a further objective of the present invention to provide a storage medium for a plurality of visual aids.

It is yet a further objective of the present invention to provide a method for using the aforesaid visual aids to facilitate inspection, stitching, and copying of cross-stitch patterns.

These and other objectives and advantages will become readily apparent to those skilled in the art upon closer reference to the following detailed description and accompanying drawing figures.

SUMMARY OF THE INVENTION

The aforesaid objectives are realized by a visual aid comprising a small, thin, planar, flexible, polymeric member which includes a central transparent section framed by an opaque section. While a rectilinear planar member is preferred, any shape is usable. The opaque section defines a plurality of ticks along its interior edge. (Opaque as used herein also includes translucent.) One side of the planar member includes a conventional, non-setting adhesive ply.

Each visual aid is removably mounted on a storage medium which comprises a paper planar member having at least one non-stick surface. Thus, the visual aid may be peeled from the non-stick surface of the backing member and temporarily adhered to another item. The opaque frame attracts the eye and focuses the vision on a small, selected area of the item, such as an embroidery or cross-stitch pattern.

DETAILED DESCRIPTION OF THE PREFERRED EMBODIMENT AND OPERATION OF THE INVENTION

Figure 1:
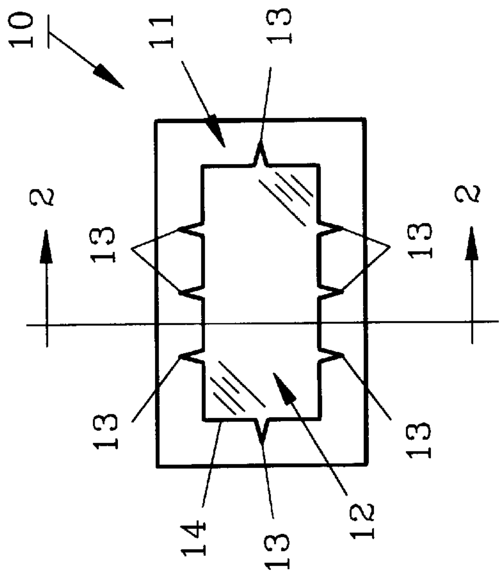
FIG. 1 shows a the preferred visual aid of the present invention.
Figure 2:
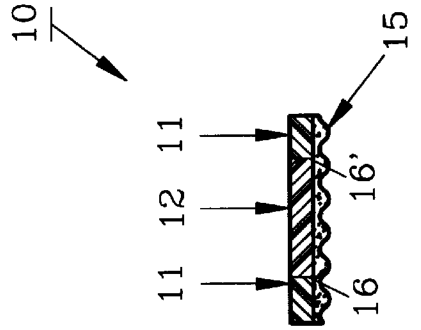
FIG. 2 depicts an enlarged cross sectional view of the visual aid, along lines 2—2 of FIG. 1.

Turning now to the drawings, specifically FIGS. 1 and 2 show preferred visual aid 10. Visual aid 10 is preferably planar, rectangular, polymeric and flexible. One acceptable material is a 2–3 mil, thick polyethylene film, although other materials and sizes are also acceptable. Opaque section 11 encircles transparent section 12. (Encircle as used herein means to surround on all sides, although non-continuous encircling is also possible.) Interior edge 14 of opaque section 11 defines a plurality of ticks 13 which are preferably wedge shaped and transparent as well. Ticks 13 are preferably located on each side of transparent section 12, but it is within the scope of the present invention to provide an opaque section 11 which only borders transparent section 12 only on one side, and thus would only define ticks 13 only on that same side. Opaque section 11 is preferably brightly colored, such as with red or yellow to attract the eye and provide an effective means to highlight a desired item, such as a specific cross-stitch, embroidering or other sewing pattern section.

As seen in FIG. 2, which is enlarged for clarity, visual aid 10 is contiguous to conventional transparent adhesive ply 15. Tacky adhesive ply 15 is similar to the adhesive used in POST-IT® notes, and allows repeated, non-setting adhesion and removal while maintaining adhesive properties. While rectangular shaped visual aid 10 is preferred, other shapes such as oval, square, elliptical or the like are contemplated. Likewise, while it is preferred to have transparent section 12 rectangular, other shapes are also possible. It should be understood that vertical lines 16 and 16' represent the borders between transparent section 12 and opaque sections 11. Visual aid 10 is a unitary integral member, and vertical lines are meant to clarify the sections in the cross-sectional view.

Figure 3:
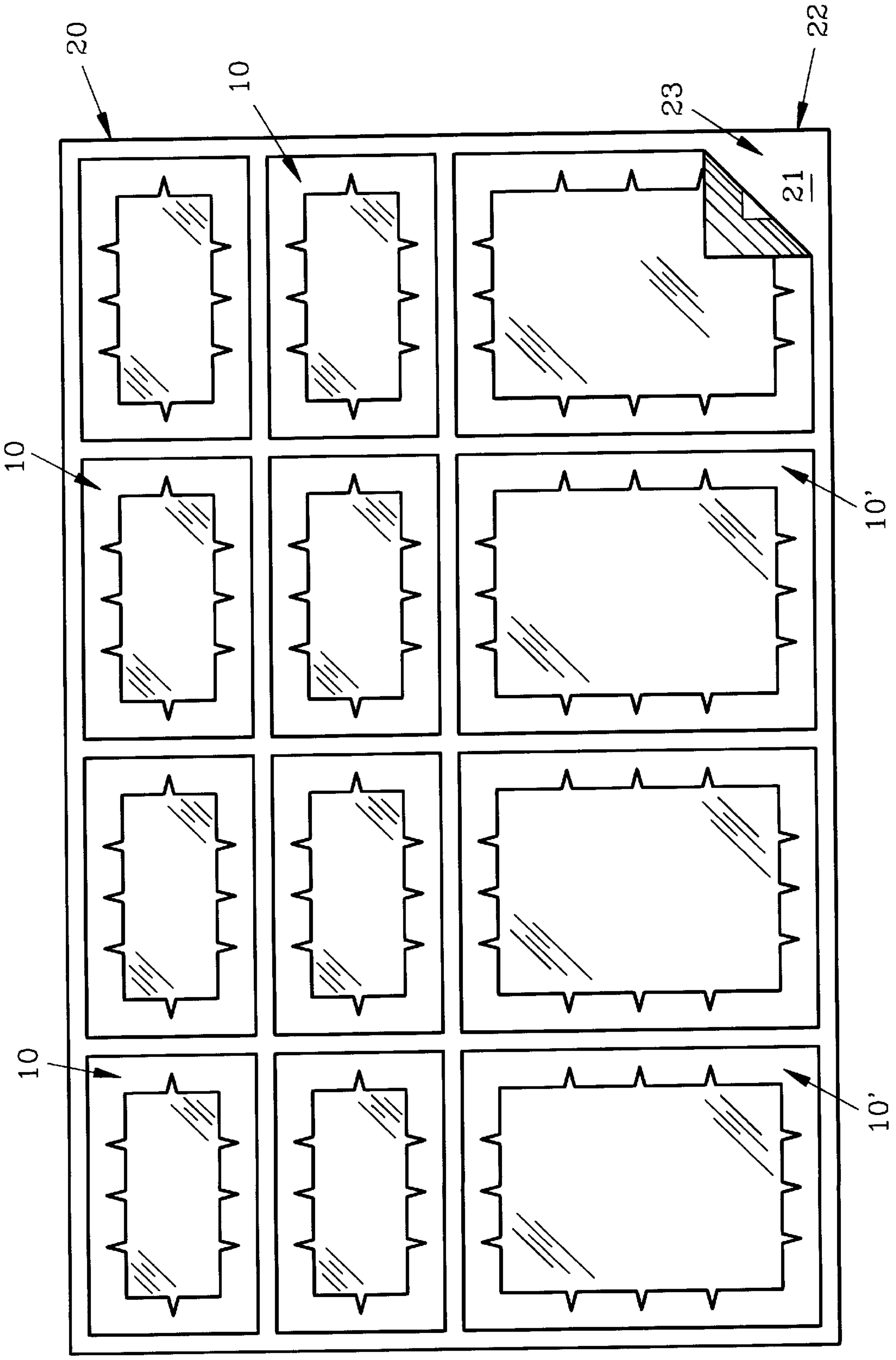
FIG. 3 illustrates a plurality of visual aids of the present invention mounted on the storage medium, with one of the larger visual aids partially removed.

Before end use, visual aid 10 is releasably mounted on backing 20 as seen in FIG. 3. Backing 20 is preferably, flexible, planar and made of thin paper. Top surface 21 on front 23 is coated with a non-stick material to facilitate peeling visual aid 10 therefrom as shown at corner 22. In practice, backing 20 is substantially larger than visual aid 10 to provide a storage medium for a plurality of visual aids 10, 10'. Note that visual aid 10' can be larger than visual aid 10 to provide visual aids for multiple sizes and uses on the same storage medium.

Figure 4:
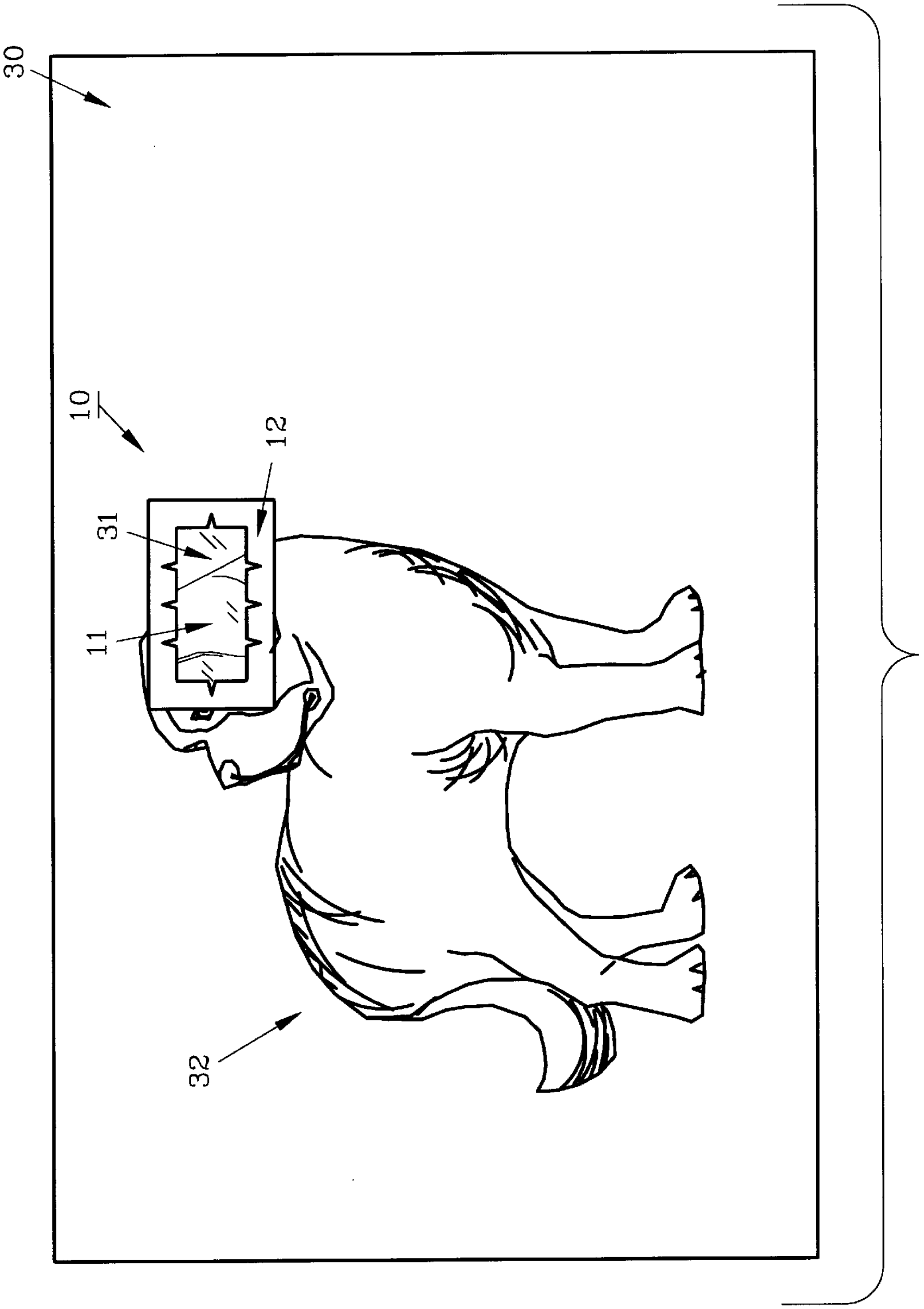
FIG. 4 demonstrates one of the smaller visual aids applied to a design of a dog.

In use, visual aid 10 are used to frame or outline part of an image on an item, such as area 31 of dog image 32 on sheet 30 (FIG. 4). Sheet 30 may be a cross-stitch or other sewing pattern which requires a user to focus on a particular area. One such item might be a "bottom line" on a financial report for highlighting (not shown). Other items, also not shown, include images on coffee mugs being transferred to another surface by paint, drawing, cross-stitch or embroidery, paint-by-numbers guide sheets or the like. In general though, area 31 constitutes substantially less than image 32 or whole sheet 30.

The preferred method of using visual aid 10 comprises selecting a portion of an image on an item, such as area 31 of image 32 on sheet 30, to be highlighted or outlined. An appropriately sized visual aid 10 can then be selected. Transparent section 12 is preferably approximately the same size as area 31 to be highlighted. Visual aid 10 is peeled from backing 20 and releasably adhered to sheet 30 by tacky, non-setting adhesive ply 15. Opaque section 11 frames and preferably continuously encircles or surrounds area 31. Ticks 13 allow the eye to easily keep track of and focus on the exact portion of area 31 which is being examined by the user while simultaneously viewing area 31. Once the user has completed his visual inspection of area 31, visual aid 10 may be manually removed from sheet 30 and repositioned over a different portion of image 32 as desired.

Visual aid 10 is particularly useful in cross-stitching where a large pattern may be used. The user peels visual aid 10 from backing 20 and adheres visual aid 10 a selected area of the pattern. The user then simultaneously views ticks 13 and highlighted part 31 while duplicating the pattern in, for example, the cross-stitch hoop. Once a particular highlighted part 31 has been embroidered, visual aid 10 is repositioned and the process repeats itself until entire image 32 has been embroidered. The user may then manually return visual aid 10 to backing 20 for later reuse as needed.

The preceding recitation is provided as an example of the preferred embodiment and is not meant to limit the nature of scope of the present invention or appended claims.

We claim:

1. A visual aid comprising:

a flexible planar member, said planar member comprising a transparent section and an opaque section, said opaque section defining a tick bordering said transparent section, said tick being transparent and continuous with said transparent section.

2. The visual aid of claim 1 further comprising an adhesive, said adhesive positioned on one side of said planar member.

3. The visual aid of claim 1 wherein said planar member is rectilinear.

4. The visual aid of claim 1 wherein said opaque section encircles said transparent section.

5. The visual aid of claim 1 wherein said tick is wedge shaped.

6. The visual aid of claim 5 wherein said opaque section continuously encircles said transparent section;

wherein said planar member is polymeric;

wherein said planar member is rectilinear; and further comprising an adhesive, said adhesive positioned on one side of said planar member.

7. A storage medium and visual aid in combination, said storage medium comprising:

a planar backing, said planar backing comprising a front, said front having a non-stick top surface; and said visual aid comprising:

a planar member, said planar member comprising a transparent section and a coplanar opaque section, said opaque section bordering said transparent section, said planar member positioned contiguous said planar backing.

8. The combination of claim 7 further comprising an adhesive ply, said adhesive ply positioned between said planar backing and said planar member.

9. The combination of claim 7 wherein said planar member is positioned on said non-stick top surface.

10. The combination of claim 7 further comprising a plurality of planar members, said plurality of planar members positioned on said planar backing.

11. The combination of claim 7 wherein said storage medium is made from paper.

12. A method of using a visual aid, said method comprising the steps of:

a) selecting a visual aid comprising a transparent section and a coplanar opaque section, b) placing the visual aid on an item to be viewed; and c) viewing part of the item through the transparent section.

13. The method of claim 12 wherein selecting a visual aid comprises the step of selecting a visual aid wherein an opaque section continuously surrounds a transparent section.

14. The method of claim 12 wherein placing the visual aid comprises the step of framing part of the item within the opaque section.

15. The method of claim 12 wherein viewing part of the item through the transparent section comprises the step of viewing part of the item through the tick.

16. The method of claim 12 further comprising the step of initially peeling the visual aid from a planar backing.

17. The method of claim 12 wherein placing the visual aid on an item to be viewed comprises the step of adhering the visual aid to an item to be viewed.

18. The method of claim 17 further comprising the step of initially peeling the visual aid from a planar backing;

wherein viewing part of the item through the transparent section comprises the step of simultaneously viewing ticks; and wherein placing the visual aid comprises the step of framing part of the item to be viewed within the opaque section.

* * * * *